United States Patent
Bayron et al.

[19]

[11] Patent Number: 5,746,199
[45] Date of Patent: May 5, 1998

[54] RESPIRATORY VALVE

[76] Inventors: Harry Bayron, 7439 Pioneer Rd., West Palm Beach, Fla. 33413; Neil Winthrop, 12A Amherst Ct., Royal Palm Beach, Fla. 33411

[21] Appl. No.: 701,085

[22] Filed: Aug. 21, 1996

[51] Int. Cl.[6] .................................................. A62B 9/02
[52] U.S. Cl. ............................. 128/205.24; 128/207.16
[58] Field of Search .......................... 128/205.24, 207.16, 128/912; 137/625.41, 625.47; 251/286, 312, 309

[56] References Cited

U.S. PATENT DOCUMENTS

| | | | |
|---|---|---|---|
| D. 271,421 | 11/1983 | Fetterman | 604/32 |
| 859,573 | 7/1907 | McMillan | 251/286 |
| 2,536,199 | 1/1951 | McDonald | 251/312 |
| 3,774,604 | 11/1973 | Danielsson | 251/309 |
| 3,780,736 | 12/1973 | Chen | 604/32 |
| 3,830,257 | 8/1974 | Metivier | 137/625.41 |
| 4,950,230 | 8/1990 | Kendell | 137/625.41 |
| 5,073,164 | 12/1991 | Hollister et al. | 604/43 |
| 5,127,398 | 7/1992 | Stone | 128/204.18 |
| 5,207,641 | 5/1993 | Allton | 604/32 |
| 5,288,290 | 2/1994 | Brody | 604/32 |
| 5,309,902 | 5/1994 | Kee et al. | 128/202.27 |
| 5,343,857 | 9/1994 | Schneider et al. | 128/202.27 |
| 5,466,228 | 11/1995 | Evans | 604/32 |
| 5,540,668 | 7/1996 | Wilson, Jr. et al. | 137/625.41 |

*Primary Examiner*—Aaron J. Lewis
*Attorney, Agent, or Firm*—McHale & Slavin

[57] ABSTRACT

A respiratory valve apparatus with a housing having a upper entry port and an opposite endotracheal tube connection port, along with a resuscitation bag connection port and an opposite respirator connection port. A rotational valve assembly with an inner channel fits within a chamber formed in the housing. The rotational assembly switches and indexably locks between two positions whereby the channel aligns the entry, endotracheal, and respirator ports in one position, and aligns the entry, endotracheal, and resuscitation ports in the second position. A guide fixture can be attached to the entry port to help steer the catheter through the apparatus. An elongated protective bag can be sealably attached around the catheter to prevent external contact with the catheter surfaces when it is withdrawn.

19 Claims, 6 Drawing Sheets

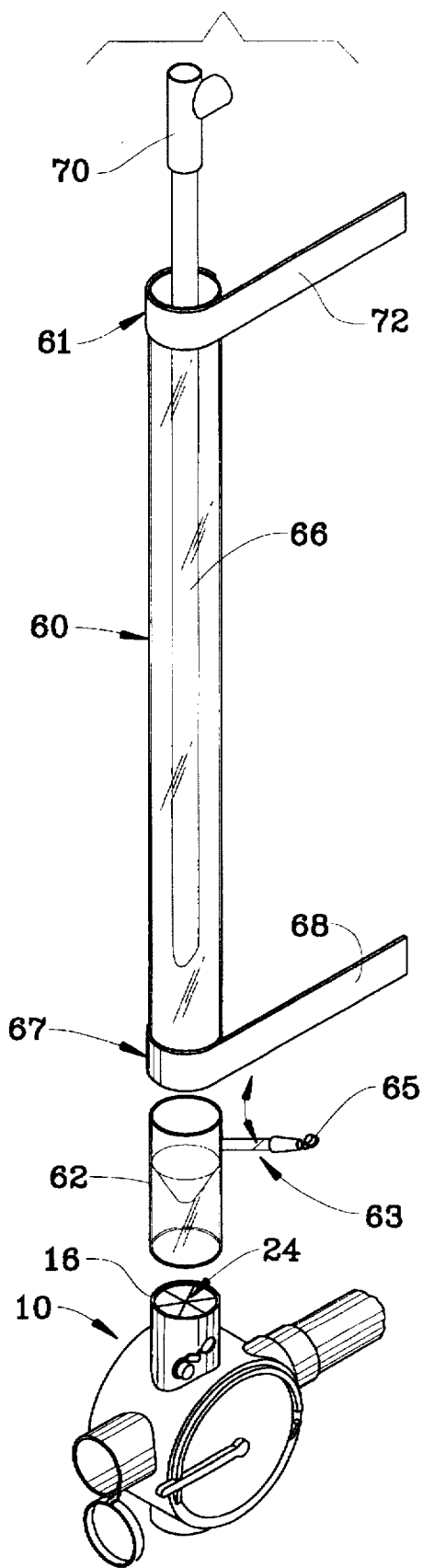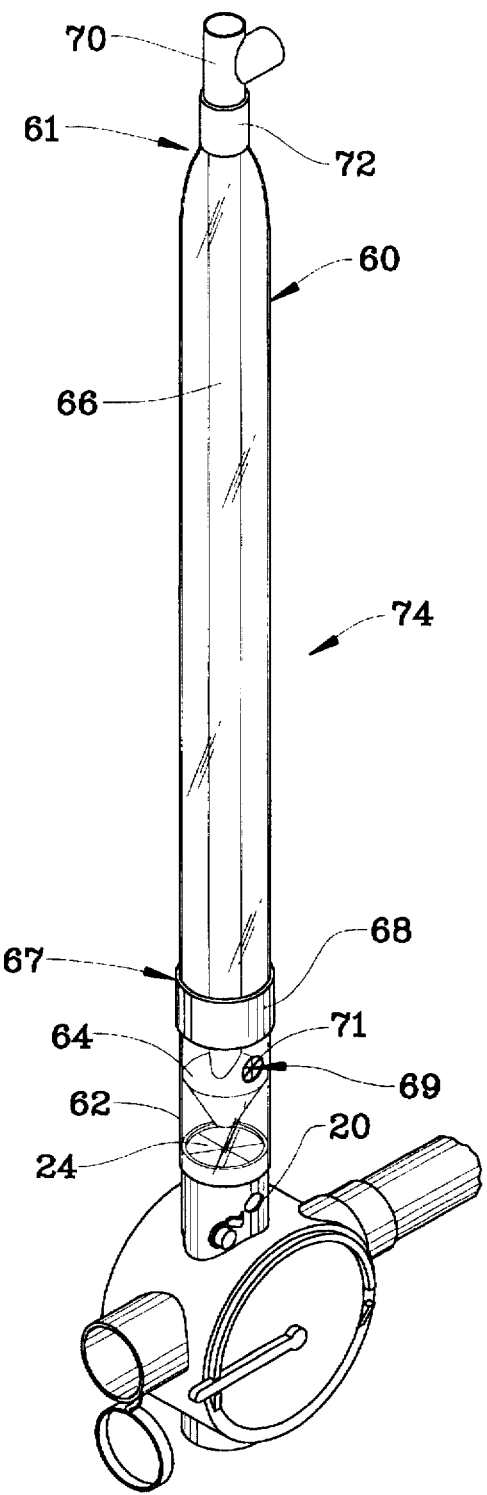

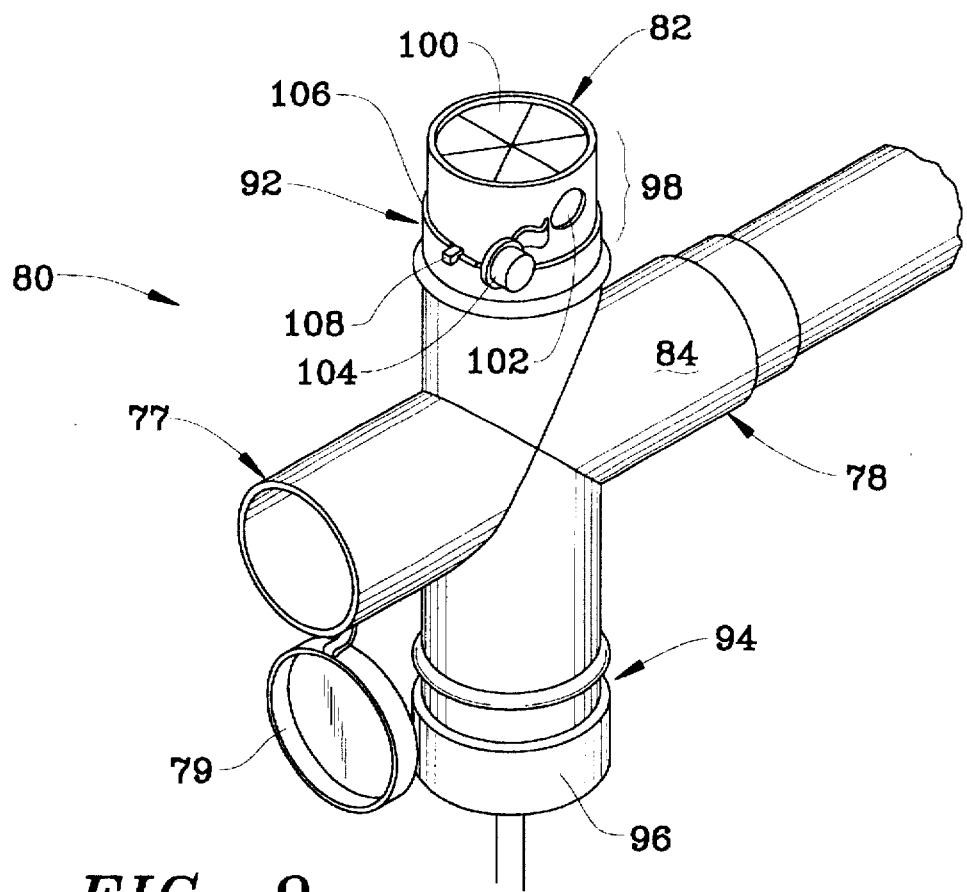
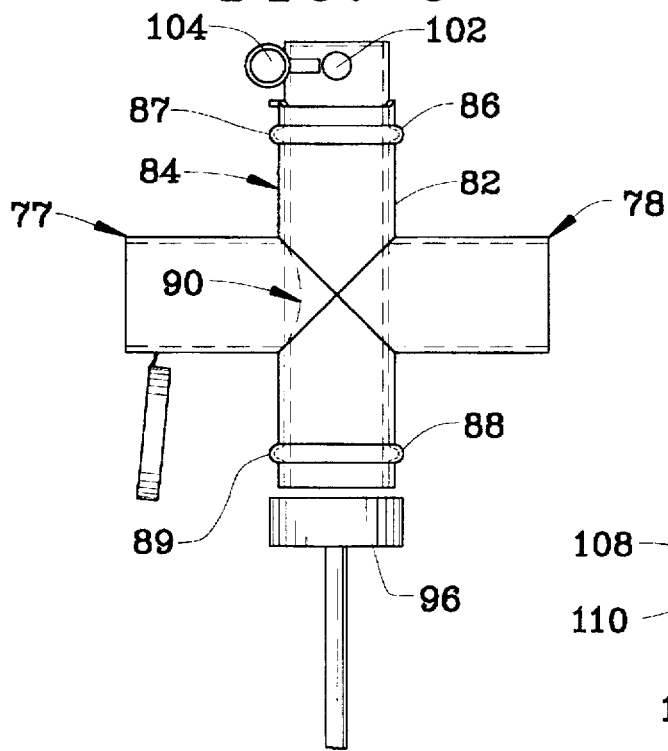
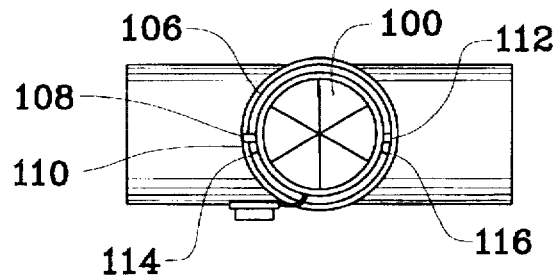

RESPIRATORY VALVE

FIELD OF INVENTION

This invention relates to respiratory valves used in endotracheal medical procedures involving a respirator, a resuscitation bag, and a suction catheter. In particular, the present invention is a respiratory valve that facilitates rapid switching between a respirator, or breathing machine, and a resuscitation bag while maintaining ventilation functions and without losing positive end expiratory pressure (PEEP), the respiratory valve permitting the withdrawal and insertion of a catheter from a sanitary self-contained enclosure for endotracheal suctioning.

BACKGROUND OF THE INVENTION

Respiratory support systems are commonly used to support the respiratory system of a critically ill patient for maintaining optimal blood oxygen levels, as well as optimal carbon dioxide levels and acid base balance. Typically, a prior art respiratory support system includes a tracheal tube, positioned either directly through the nose or mouth into the trachea of a patient. A multi-ported manifold is connected to the endotracheal tube at one port position, and a source of breathable gas is connected at a second port. The respiratory support system assists the patient in maintaining adequate blood oxygenation levels without overtaxing the patient's heart and lungs.

While a patient is attached to the respiratory support system, it is periodically necessary to aspirate fluids and or secretions from the patient's trachea and lungs. In the past, in order to accomplish aspiration, it was necessary to disassemble part of the respiratory support system, either by removing the ventilator manifold or by opening a port thereof and inserting a small diameter suction tube down the tracheal tube and into the patient's trachea and lungs. The fluid was then suctioned from the patient and the suction catheter was removed and the respiratory support system reassembled. However, due to the interruption of respiratory support during this procedure, a patient's blood oxygen can often drop and the carbon dioxide can change to unacceptable levels. Additionally, unless a sufficient positive end expiratory pressure (PEEP) level is maintained, then the lungs might collapse. This creates a dangerous condition for the patient because the lungs can be difficult, and sometimes impossible, to reinflate.

Patients may have fluid drawn from their lungs as often as six times a day and sometimes more, possibly over long periods of time. For this reason, it is critical to provide a respiratory device which will minimize patient discomfort. In addition, such a device could be widely used in treating pediatric patients, especially premature infants who are subject to respiratory problems and may need frequent aspirations. As a result of the extremely large number of aspirations necessary on various patients in any period, it is important that the price of the respiratory device be as low as possible since vast numbers will be used. It is also important that the device be sufficiently inexpensive so that it may be discarded after a single use. Hence, it is desirable to simplify such devices and reduce the number of parts in order to reduce costs and increase reliability.

Prior art devices have attempted to maintain a continuous flow of oxygen from the respirator device through to the lungs, while allowing for insertion and retraction of the suction catheter. However, such devices fail to provide an operable system capable of performing both manual and machine assisted respiration without disconnecting the respirator. Manual respiration with a resuscitation bag is a preferred method among many practitioners because it optimizes removal of fluids in the lungs while maintaining PEEP and maintaining cardiopulmonary and hemodynamic balance. U.S. Pat. No. 4,351,328 discloses a device for simultaneous respiration and endotracheal suctioning of a critically ill patient. This device requires a specialized sealing port for insertion and retraction of the suction catheter to maintain the integrity of the respiration system. While machine assisted respiration is occurring, no switchover to manual resuscitation methods is provided.

U.S. Pat. No. 5,343,857 discloses an accessory port capable of receiving a specially designed male adaptor on a suction catheter. The accessory port consists of a normally closed valve which is forced open by the male adaptor, and returns to its closed position upon retraction of the adaptor. The adaptor sealably interacts with the accessory port so as to inhibit pressure loss from the manifold. A similar device is disclosed in U.S. Pat. No. 5,309,902.

As detailed in the background discussions of these prior art disclosures, there are many difficulties associated with maintaining continuous pressure from the respiration supply device. More particularly, it is often desirable to be able to manually inflate the lungs with a resuscitation bag at different rates and different volumes in order to facilitate complete aspiration of mucous and liquid from the lungs. With the extra "hands-on" control offered by the resuscitation bag, a doctor or technician can simulate expectory coughing actions and the like through quick inflation and deflation bursts. Moreover, PEEP can be easily maintained with the resuscitation bag, while the suction catheter is repeatedly inserted and retracted from the lungs as needed.

Other interface devices require the respirator source to be disconnected in order to attach the desired resuscitation bag. Once aspiration is complete, this presents a problem with maintaining PEEP when the resuscitation bag is disconnected and the respirator source is reconnected. Even if performed in a timely and efficient manner, this switchover operation can jeopardize the patient's life if PEEP is not maintained. Hence, it is important to minimize this switchover time, while also providing for attachment of the resuscitation bag. Other devices remain connected to the respirator source and do not allow for use of a resuscitation bag.

U.S. Pat. No. 5,207,641 discloses a switching device with a rotary valve having aspiration, insufflation, and intermediate flushing positions. An oxygen port and suction port are included with a catheter port. These ports allow suction and insufflation to alternately occur through the continuously inserted catheter, without withdrawal of the catheter tube from the lungs. While providing a neutral valve position, this arrangement might still encounter problems such as blowback of mucous through the inserted catheter, and/or clogging of the valve parts by suctioned mucous.

U.S. Pat. No. 3,780,736 discloses a surgical valve assembly for urinary bladder irrigation and drainage. This valve has four ports and provides a core for interconnecting any two of the four ports. The core allows irrigation fluids to flow from one port to another, but the '736 device does not disclose a valve for introduction and withdrawal of a suction catheter through the device in either of two switched positions, and the '736 device does not disclose ports for receiving air from a respirator in one switched position or alternatively from a resuscitation bag in the other switched position.

Given the frequent insertion and withdrawal of the suction catheter, a protective bag, or sleeve, would also be a useful addition to existing suction catheter devices. This bag would prevent external contact with the catheter thereby maintaining a sterile device for reinsertion into the patient. U.S. Pat. No. 5,073,164 discloses a specialized catheter which incorporates a protective sleeve. A bag which can be sealably attached around any existing suction catheter would be even more versatile than the incorporated sleeve.

Accordingly, what is lacking in the art is a respiratory valve device which can accommodate the introduction of a suction catheter into a patient's lungs while maintaining connection with an external respirator source, and which will subsequently allow uninterrupted respiratory switchover to a resuscitation bag to maintain optimal ventilation. An attachable bag and associated attachment fixture should be provided which protects the withdrawn catheter during switchover of the valve and otherwise.

SUMMARY OF THE INVENTION

The present invention provides a respiratory valve apparatus with a housing having an inner rotating assembly which can be rotated between two switching positions. The first position allows a flow-through connection between a patient and an external respirator support system. The second position provides a flow-through connection to a resuscitation bag. A patient can thereby receive continuous support from a respirator support or an attached resuscitation bag, depending upon the position of the valve. The valve assembly provides a port with a sealing orifice for insertion and retraction of a suction catheter through the valve assembly and into the patient's lungs as needed. The resuscitation bag may be preferable over a continuous respirator support system connection because of added control over lung inflation provided. Many operators prefer the greater endotracheal and lung clearing results that can be achieved by simulating coughing attained through the use of the resuscitation bag. By providing an efficient switchover between the respirator and resuscitation bag, a patient can be treated in such a manner without having to disconnect the respirator support system to thereby connect the resuscitation bag. This prevents the loss of positive end expiratory pressure (PEEP) in the lungs and guards against lung collapse and hemodynamic compromise.

The apparatus additionally utilizes a protective bag designed to fit around any suction catheter and prevents outside contact with the catheter when it is withdrawn from the patient. This eliminates the need to constantly change-out the catheter if it touches external objects and becomes contaminated. A fixture is included which fits over the suction catheter port and has an inner conical surface to help guide the catheter through the more flexible center part of the suction port orifice. The bag would be sealed around the fixture and around the upper part of the catheter via strips of adhesive tape or any other such material. The bag might also be bonded directly to the fixture and to the suction catheter. The fixture also includes a saline flush port.

Additional features might include a hingably attached cover for the resuscitation bag port when a resuscitation bag is not attached. An endotracheal tube would also be removably attached to the valve assembly body to guide the catheter downwards into the patient's lungs. A hingable covered or sealable port for injection of saline into the valve assembly would allow the parts to be rinsed as needed. Additionally, the rotating inner assembly would have a lockable access handle and rotation method to insure proper positioning with respect to the assembly ports and to prevent accidental interruption of ventilation.

It is therefore an object of the present invention to provide a respiratory valve apparatus which can switch between an attached external respirator support system and an attached resuscitation bag, and can accommodate insertion of a suction catheter through the apparatus when placed in either switched position.

It is a related object of the present invention to provide a respiratory valve apparatus having a housing with a suction catheter entry port, a endotracheal tube connection port, a respirator connection port, and a resuscitation bag connection port.

It is still another object of the present invention to provide an inner rotational assembly insertably contained within the apparatus housing which connects the respirator port with a channel between the entry port and endotracheal tube port in a first switched position, and which connects the resuscitation bag port with the channel in the second switched position.

It is yet another object of the present invention to provide a sealable orifice in the catheter entry port which seals upon withdrawal of the catheter.

It is yet another object of the present invention to provide a lockable rotation handle which has positive indexing of its switching positions and which prevents improper rotation of the inner rotatable fixture.

It is still another object of the present invention to provide a hingably attached cover for the resuscitation bag port for sealably covering the port when a bag is not attached.

It is yet another object of the present invention to provide a hingably covered or sealable saline port in the housing assembly for injecting saline to clean the valve assembly parts.

It is still another object of the present invention to provide an elongated bag which can be sealed around any of a variety of suction catheters, the bag sealably covering and protecting the catheter, the bag tapably sealed at its lower end around a guiding fixture which fits onto the catheter entry port, and the bag tapably sealed at its upper end around an upper portion of the catheter. Other methods of adhering the bag around the cather and fixture are also intended to be used.

Other objects and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

FIG. 5 shows a perspective view of the respiratory valve assembly with an exploded view of the catheter entry port guide fixture and protective bag which is sealably taped around the catheter.

FIG. 6 shows a perspective view of the respiratory valve assembly of FIG. 5 with the guide fixture and protective bag attached.

FIG. 8 shows a perspective view of another embodiment of the respiratory valve assembly which has an inner rotational cylinder.

FIG. 9 shows a front view of the respiratory valve assembly of FIG. 8.

FIG. 10 shows a top view of the respiratory valve assembly of FIG 8.

DETAILED DESCRIPTION OF THE PREFERRED EMBODIMENT

Although the invention has been described in terms of a specific embodiment, it will be readily apparent to those skilled in this art that various modifications, rearrangements and substitutions can be made without departing from the spirit of the invention. The scope of the invention is defined by the claims appended hereto.

Figure 1:
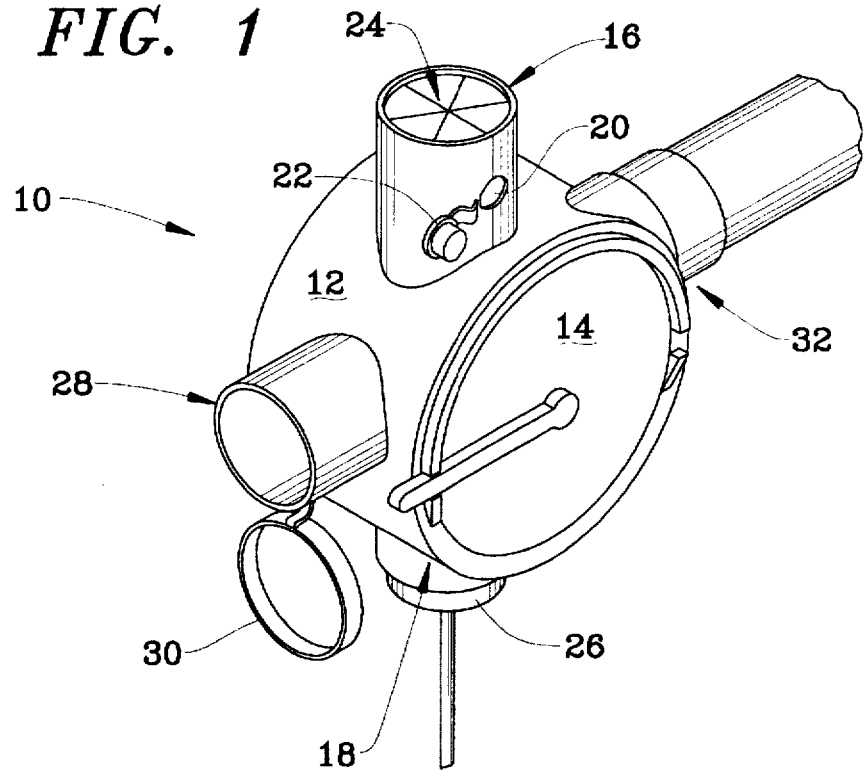
FIG. 1 shows a perspective view of the respiratory valve assembly.
Figure 1A:
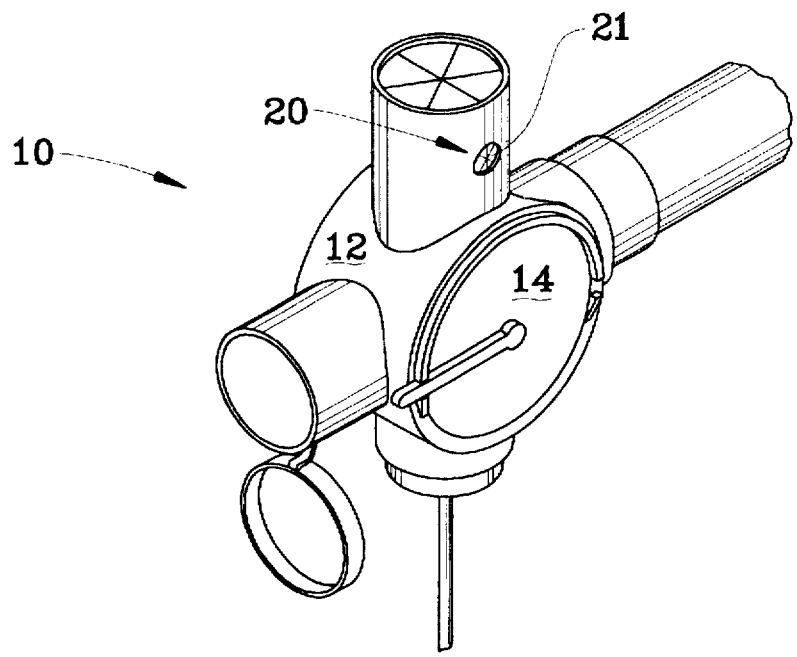
FIG. 1A shows a perspective view of a smaller version of the respiratory valve assembly as similar to FIG. 1, with the center rotational assembly scaled down in relation to the various ports.
Figure 2B:
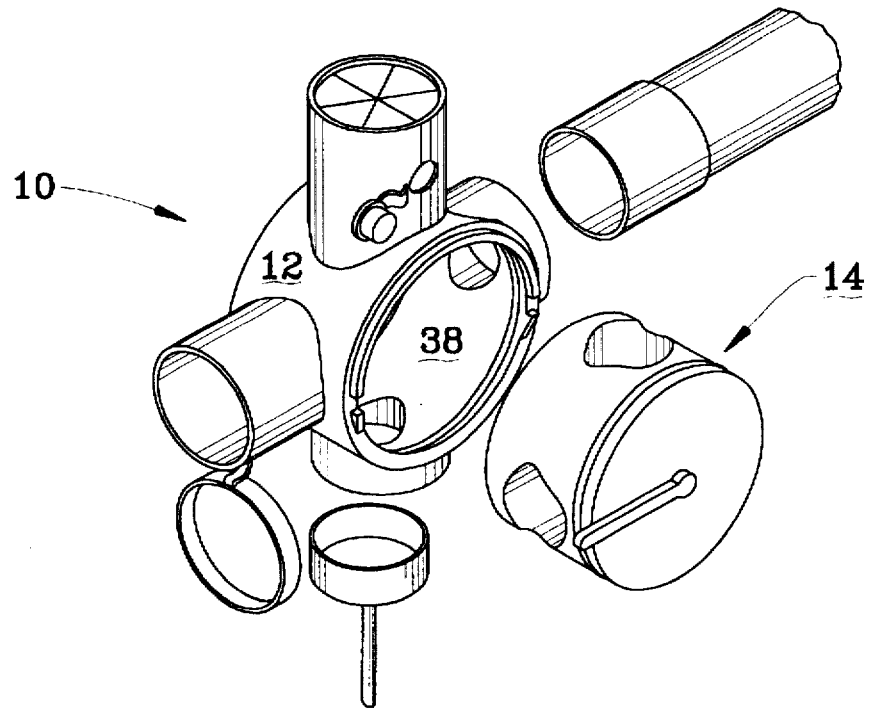
FIG. 2A shows an exploded perspective view of a smaller version of the respiratory valve assembly as similar to FIG. 2, with the center rotational assembly scaled down in relation to the various ports.

Referring now to FIG. 1, a perspective view of the respiratory valve assembly 10 is shown. The assembly has a housing 12 and an inner rotational valve assembly disk 14. This disk 14 is cylindrical in shape. The housing 12 includes an upper access port which is a suction catheter entry port 16 located on the top and a endotracheal tube connection port 18 located on the bottom. The entry port 16 has a flexible orifice 24 covering the top and additionally includes a saline injection port 20 which can be covered by a hingably attached plug 22. Port 20 might alternatively use a sealable orifice 21 as shown in FIG. 1A, or a saline injection port line shown as 63 in FIG. 5. An endotracheal tube 26 can be removably attached to the endotracheal connection port 18. A resuscitation bag attachment port 28 extends out one side, oriented generally 90 degrees from the entry port 16 and endotracheal tube connection port 18. This port 28 can be sealably covered by a hingably attached cover 30. On the opposite side of the bag attachment port 28 is a respirator attachment port 32 for attaching an external respirator device.

Figure 2:
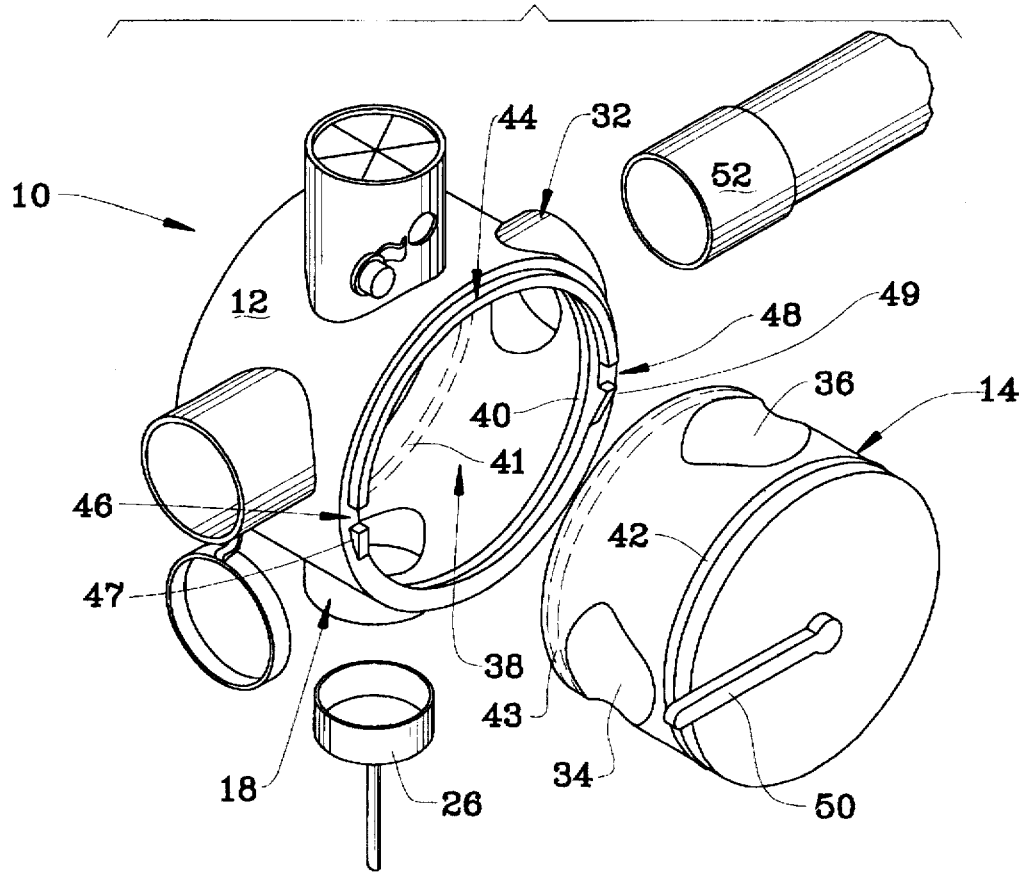
FIG. 2 shows an exploded perspective view of the respiratory valve assembly.

Referring now to FIG. 2, an exploded perspective view of the respiratory valve assembly 10 is shown. In this view, the inner rotation valve assembly disk 14 is shown to be cylindrical or disk-like in shape with inlets 34 and 36 connected by channels which are more clearly shown in FIG. 3. The assembly disk 14 fits into a cavity or chamber 38 which is formed in the center of the housing 12. To facilitate secure insertion of the assembly disk 14, a circumferential groove 40 is formed around the surface of the chamber 38. A corresponding circumferential ridge 42 is formed around the assembly disk 14. Alternatively, a second circumferential ridge 43 and a corresponding groove 41, both shown in fathom, might be formed around the assembly disk 14 and chamber 38. When the assembly disk 14 is inserted into the chamber 38, this groove 40 mates with the ridge 42 so that the assembly disk 14 securely snaps into place and seals from loss of gas pressure. If provided, the second ridge 43 additionally snaps and seals into groove 41. The rotational movement is then guided by this groove and ridge mating.

The housing 12 additionally has a semi-circular lip 44 which protrudes from the front of the housing. This lip 44 has a first indexing slot 46 and a second indexing slot 48, with the lip 44 ramping down to the face of the housing thereafter via ramps 47 and 49 on either side. On the front of the assembly disk 14 is a handle 50 which is flexible enough to bend up and over the ramps 47 and 49 to fall into the indexing slots 46 and 48. When snapped into place, the assembly disk 14 can be rotated via the handle 50 to one of two switching positions which align the ports and disk channels as needed The lip 44 allows the disk 14 to be rotated in one direction with the handle moving around the bottom arc of the circular front of the housing 12.

This exploded view also more clearly shows the endotracheal tube 26 which detachable fits onto the connection port 18 and guides a suction catheter into the patient after it has been inserted into and through the respiratory valve assembly 10. The external respirator connection 52 is also shown which attaches to the respirator connection port 32.

Referring now to FIG. 1A, a perspective view of an alternative embodiment of the respiratory valve assembly 10 of FIG. 1 is shown. Referring also to FIG. 2A, an exploded view of this alternative embodiment is shown as similar to FIG. 2. This embodiment differs only in that the size of the central part of the housing 12 is smaller than in FIGS. 1 and 2. Accordingly, the assembly disk 14 and the chamber 38 will be correspondingly smaller. This smaller embodiment would be extremely useful when working with infants and children. The inventors intend that all such size variations with respect to the respiratory valve assembly parts are encompassed within the scope of this invention.

Figure 3:
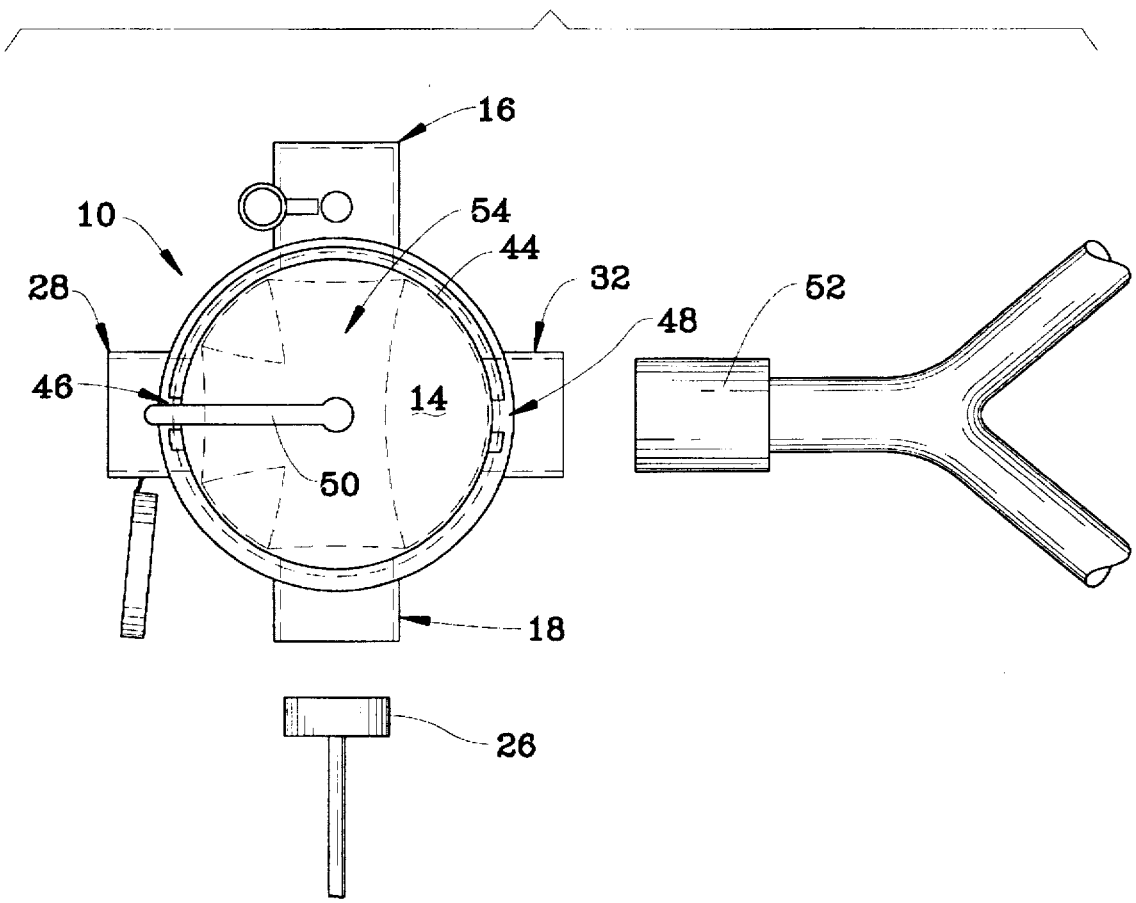
FIG. 3 shows a front exploded view of the respiratory valve assembly.

Referring now to FIG. 3, a front view of the respiratory valve assembly 10 is shown. This view shows, via phantom lines, the inner channel 54 which runs inside the inner rotational assembly disk 14. This T-shaped channel 54 provides a conduit between the entry port 16 and endotracheal tube connection port 18 whereby a suction catheter can be inserted through the valve assembly 10. The T-shaped channel 54 opens towards the port 28 or 32 in which the handle 50 is pointing. In the switching position shown, the handle 50 is locked into index 46 in lip 44. A resuscitation bag, not shown, can be attached to the resuscitation bag port 28. With the endotracheal tube 26 attached to the connection port 18, the respiratory valve assembly 10 could be positioned over a patient's mouth with the endotracheal tube extending into the patient. A catheter could be inserted through the T-shaped inner channel 54, and the resuscitation bag could be used to manually provide volumetric units of air into the patient's lungs. By skillfully combining the manual inflation actions with the suction catheter procedure, optimum clearing of the lungs can be accomplished.

With the respirator connection 52 attached to the respirator attachment port 32, the catheter can be withdrawn and the disk assembly 14 can be rotatably switched to the opposite setting whereby the handle 50 is pointing towards the attachment port 32. The handle 50 would then be locked into index position 48 in lip 44. Accordingly, the respirator connection 52 will now be breathably connected to the patient without loss of PEEP in the patient's lungs. The suction catheter can then be reinserted and withdrawn as needed through the assembly 10.

Figure 4:
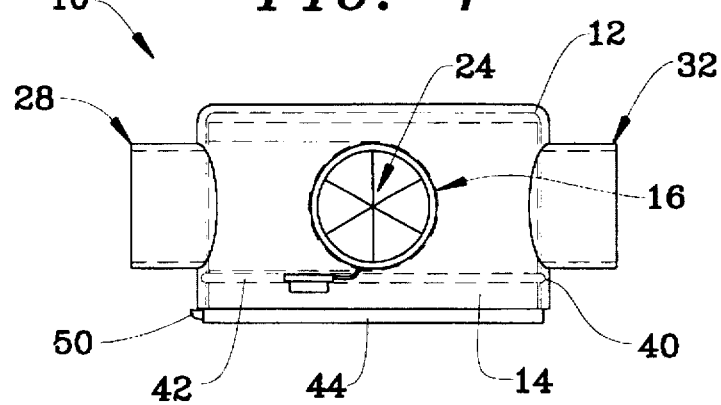
FIG. 4 shows a top view of the respiratory valve assembly.

Referring now to FIG. 4, a top view of the respiratory valve assembly 10 is shown. The flexible orifice 24 is shown covering the catheter entry port 16. The inner assembly disk 14 is shown in fathom. This view also shows a top-down angle of the circumferential ridge 42 which extends around the assembly disk 14 and snaps into the corresponding groove 40 in the housing 12. The lip 44 forms a semi-circular barrier around the upper front portion of the housing 12. The end of the handle 50 is shown protruding out from the side of the housing 12. This protruding end provides a leverage point for prying the flexible handle out from the indexing slot 46 or 48. The handle 50 is then allowed to slide down the ramps, not shown in this view, and thereby allow the assembly disk 14 to be rotated.

Referring now to FIG. 5, a perspective view of the respiratory valve assembly 10 is shown with an exploded view of the additional bag-like attachment 60 and an attachment fixture 62. The attachment fixture 62 is tubular in shape and removably attaches, via snug frictional contact or otherwise, with the catheter entry port 16. While the preferred embodiment would likely be constructed of opaque plastic, a transparent version of the attachment fixture 62 shows an inner conical guide 64 which steers an inserted catheter down through the center portion of the orifice 24. This eases catheter insertion through the orifice 24 because the center part of the orifice is more flexible and less resistant than the edges. The bag-like attachment 60 is threaded over the suction catheter 66 and the bottom end 67 of the bag is secured around the fixture 62 with a strip of seal forming adhesive tape 68, or other such materials. The upper end 61 of the bag 60 is secured around the upper attachment fixture 70 by another strip of seal forming adhesive tape 72. Also shown is a saline adaptor port 63 for flushing out the system which extends outwards for convenient access and has a hingably attached cover 65. In lieu of, or in addition to, the hingably attached cover 65, the port 63 might include a bendable, or hingable flap 75 within the extension tube which would allow for injection of saline in one direction, and which would spring back into position to prevent further escape of gas and/or fluids when the saline injection device is withdrawn.

Referring now to FIG. 6, a perspective view of the assembled device 74 is shown. The guide fixture 62 fits over the entry port 16 so as not to block the saline injection port 20. The adhesive tape strip 68 wraps around and secures the bottom bag end 67 to the fixture 62. The conical guide section 64 is then placed over the center of the orifice 24. The upper end 61 of the bag 60 is sealably constricted around the upper attachment fixture 70 via the adhesive tape strip 72. This guide fixture 62 shows an alternative saline port 69 which is located flush on the side of the fixture 62 and which uses a sealable orifice 71. Any saline port configuration can be used as appropriate.

Figure 7:
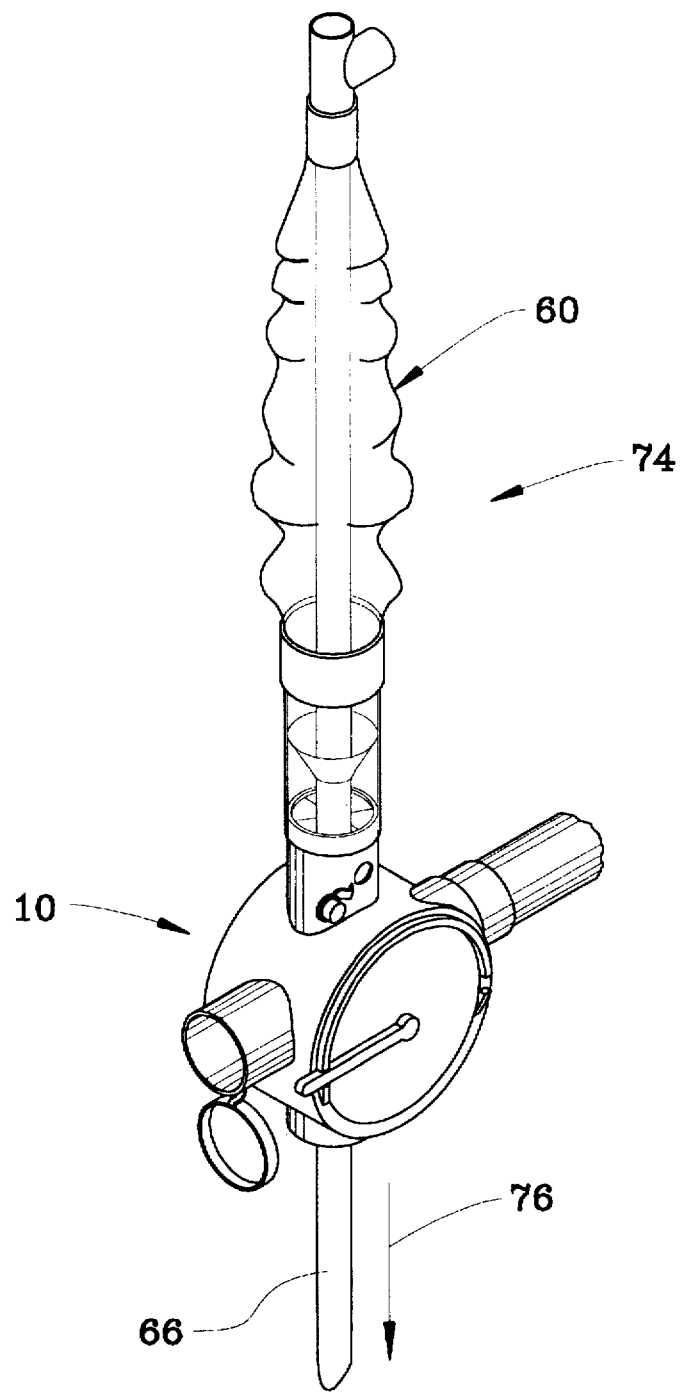
FIG. 7 shows a perspective view of the respiratory valve assembly of FIG. 6 with the suction catheter inserted through the valve assembly and the protective bag foldably compressed.

Referring now to FIG. 7, a perspective view of the assembled device 74 is shown in operation. As shown by the arrow 76; the suction catheter 66 is advanced downward through the respiratory valve assembly 10. As the catheter 66 is advanced, the bag 60 folds and crumples depending upon how far the catheter is advanced. Upon withdrawal of the catheter 66, the bag 60 unfolds, and yet remains sealably attached around the catheter 66 to prevent contact or contamination from outside sources. Because this bag 60 is sealably taped around the catheter 66 and the guide fixture 62, it can be interchangeably used with any of a variety of suction catheter products.

FIGS. 8 through 10 show an alternative embodiment of the respiratory valve assembly 80 which uses an inner tubular cylinder 82 which fits inside the inner chamber of the valve housing 84. This cylinder 82 provides a rotational valve assembly which spins around its vertical axis to provide alternate access between the resuscitation bag connection port 77 with a hingably attached cover 79, and the respirator attachment port 78. The cylinder 82 would be inserted through the top of the housing 84 and would snap into place to provide free-spinning action. The upper access port 92 thereby serves as a cylinder insertion port with the suction catheter being inserted through the central portion of the cylinder, through to the exit port 94 and attached endotracheal tube 96. The top portion 98 of the cylinder 82 extends upwards to provide a gripping surface for spinning the cylinder. A sealable orifice 100 extends across the top of the cylinder 82. A saline injection port 102 is provided in the cylinder top portion 98 and further includes a hingably attached plug 104. As with the previous embodiment, this port could also include a sealable orifice thereby eliminating the need for the hingably attached plug.

FIG. 9 shows the mounted cylinder 82, in fathom, through the housing 84. In this embodiment, a first cylindrical ridge 86 and a second cylindrical ridge 88 extend around the upper and lower portions of the upright cylinder. These ridges interface with a corresponding first groove 87 and second groove 89. When the cylinder 82 is inserted into the housing 84 with sufficient pressure, these ridges and grooves snappably interface to securely, yet spinably, retain the cylinder in the housing. While shown pronounced in these drawings, such ridges and grooves could also be relatively minimal in size to allow easier insertion of the cylinder into the housing, while still providing secure retainment. Also, the assembly 80 might function with only a single ridge/groove combination, or alternatively a flexible or springing catch, not shown, as known in the art. This catch would extend into the corresponding groove and provide guidance and retainment of the spinning cylinder.

The cylinder 82 can thereby be rotated, or switched between two switching positions using a method similar to the previous embodiment. Referring also to FIG. 10, the cylinder insertion port 92 includes a semi-circular lip 106 with indexing positions 110 and 112, and ramped sections 114 and 116. A flexible handle 108 extends out from the cylinder and interfaces with these indexing positions as in the previous embodiment to lock the cylinder into its first and second switched positions.

Referring again to FIG. 9, the cylinder 82 is shown to have a port access hole 90 in its side. The hole aligns with the respirator attachment port 78 in the first switching position, and aligns with the resuscitation bag connection port 77 in the second switching position. In operation, the suction catheter is thereby inserted through the orifice 100, through the cylinder 82 and into the endotracheal tube 96. The cylinder can be switched and locked into a first indexed position 112 to allow ventilation with an external respirator. Alternatively, the cylinder can be rotated and locked into a second indexed position 108 to allow ventilation with an attached resuscitation bag.

While not shown in FIGS. 8–10, the bag-like attachment 60 detailed in FIGS. 5–7 can also be used with this embodiment. The guide fixture 62 would fit over the exposed upper portion 98 of the mounted cylinder 82, but without blocking the saline port 102. As before, the bag would then be attached, via adhesive tape or otherwise, to the guide fixture 62 and to an upper attachment fixture 70 of the suction catheter 66. With this second embodiment, the entire guide fixture 62 and attached bag 60 would thereby rotate with the spinning cylinder between switching positions.

With each of the aforementioned embodiments the user will typically remove the suction catheter before switching from one ventilation position to another. The embodiment using the rotating cylinder has the added advantage over the previous embodiment in that the suction catheter does not have to be removed in order to switch the valve from one ventilation position to another. The suction catheter might optionally be left extended through the valve assembly during switching, or removed, depending upon the preference and needs of the operator.

It is to be understood that while certain forms of the invention are illustrated, it is not to be limited to the specific forms or arrangements of parts herein described and shown. It will be apparent to those skilled in the art that various changes may be made without departing from the scope of the invention and the invention is not to be considered limited to what is shown in the drawings and descriptions.

What is claimed is:

1. A respiratory valve apparatus comprising:
   a housing having an inner chamber, an upper access port and an opposite endotracheal tube connection port, a respirator connection port and an opposite resuscitation bag connection port, and first and second indexing slots defining first and second switching positions;
   a rotational valve assembly which rotatably fits inside said housing chamber, said assembly having an inner channel and an outwardly facing handle which locks into said indexing slots, said channel being aligned with said entry, endotracheal, and respirator ports in said first switching position, and said channel being aligned with said entry, endotracheal, and resuscitation ports in said second switching position;
   wherein a suction catheter can be inserted through said apparatus in either of said switching positions.

2. The respiratory valve apparatus of claim 1, wherein said rotational valve assembly is cylindrically shaped with an outer cylindrical surface, said rotational valve assembly including at least one circumferential ridge around the outer cylindrical surface, said housing including a corresponding circumferential groove around its inner cavity, said ridge and said groove interacting to receivably contain said rotational valve assembly in said chamber of said housing.

3. The respiratory valve apparatus of claim 2, wherein said cylindrical rotational valve assembly is disk shaped with an outer and inner face and a flexible handle extending from its outer face, said housing having a front face with said inner chamber formed therein for receiving said disk, and said upper access port of said housing being a catheter entry port.

4. The respiratory valve apparatus of claim 3, wherein said housing front face includes a semi-circular lip with cutouts forming said first and second indexing slots and first and second ramps sloping down to said housing front face after said cutouts, said handle flexing over said ramps and into said cutouts as said valve assembly is rotated into said switching positions.

5. The respiratory valve apparatus of claim 3, wherein said catheter entry port includes a sealable orifice which allows entry of said suction catheter and which seals upon retraction of said catheter.

6. The respiratory valve apparatus of claim 3, which further includes an elongated protective bag with an upper and lower end, and an entry port guiding fixture, said guiding fixture fitting onto said catheter entry port and containing a conically shaped inner surface for guiding said catheter into said apparatus, said lower end of said protective bag being sealably attached to said guiding fixture, and said upper end of said protective bag being sealably attached to an upper end of said catheter.

7. The respiratory valve apparatus of claim 6, wherein said bag is sealably attached using adhesive tape strips.

8. The respiratory valve apparatus of claim 2, wherein said cylindrical rotational valve assembly is tubularly shaped with an extended upper open portion, an open lower portion, and a side hole, said upper access port of said housing providing access to said inner chamber for spinably mounting said tubular cylinder.

9. The respiratory valve apparatus of claim 8, wherein said extended upper portion has a flexible handle extending from said outer cylindrical surface, said upper access port including a semi-circular lip with cutouts forming said first and second indexing slots and first and second ramps sloping down to said port after said cutouts, said handle flexing over said ramps and into said cutouts as said valve assembly is rotated into said switching positions.

10. The respiratory valve apparatus of claim 8, wherein said upper tubular opening includes a sealable orifice which allows entry of said suction catheter and which seals upon retraction of said catheter.

11. The respiratory valve apparatus of claim 8, wherein said rotational valve assembly includes a saline injection port with a hingably attached port plug.

12. The respiratory valve apparatus of claim 8, wherein said rotational valve assembly includes a saline injection port with a sealable orifice.

13. The respiratory valve apparatus of claim 8, which further includes an elongated protective bag with an upper and lower end, and an entry port guiding fixture, said guiding fixture fitting onto said extended upper portion of said tubular cylinder and containing a conically shaped inner surface for guiding said catheter into said apparatus, said lower end of said protective bag being sealably attached to said guiding fixture, and said upper end of said protective bag being sealably attached to an upper end of said catheter.

14. The respiratory valve apparatus of claim 13, wherein said bag is sealably attached using adhesive tape strips.

15. The respiratory valve apparatus of claim 1, wherein said endotracheal connection port includes an endotracheal tube which can be removably attached.

16. The respiratory valve apparatus of claim 1, wherein said resuscitation bag connection port includes a hingably attached port cover.

17. The respiratory valve apparatus of claim 1, wherein said housing assembly includes a saline injection port with a hingably attached port plug.

18. The respiratory valve apparatus of claim 1, wherein said housing assembly includes a saline injection port with a sealable orifice.

19. A respiratory valve apparatus comprising:
   a housing having an inner chamber, a upper entry port and an opposite endotracheal tube connection port, a respirator connection port and an opposite resuscitation bag connection port, and first and second indexing slots defining first and second switching positions;
   a rotational valve assembly which rotatably fits inside said housing chamber, said valve assembly having an inner channel and an outwardly facing handle which locks into said indexing slots, said channel being aligned with said entry, endotracheal, and respirator ports in said first switching position, and said channel being aligned with said entry, endotracheal, and resuscitation ports in said second switching position;
   an elongated protective bag with an upper and lower end;
   an entry port attachment fixture removably fitting onto said catheter entry port and containing a conically shaped inner surface for guiding said catheter into said apparatus an endotracheal tube removably fitting onto said endotracheal tube connection port for guiding said catheter into the patient;

wherein said lower end of said protective bag is sealably attached to said guiding fixture, and said upper end of said protective bag is sealably attached to an upper end of said catheter, thereby allowing said catheter to be inserted through said apparatus in either of said switching positions with said protective bag preventing external contact with said catheter when it is withdrawn.

* * * * *